(12) United States Patent
Brazdil et al.

(10) Patent No.: US 8,084,388 B2
(45) Date of Patent: Dec. 27, 2011

(54) CATALYST COMPOSITION AND PROCESS FOR THE SELECTIVE OXIDATION OF ETHANE AND/OR ETHYLENE TO ACETIC ACID

(75) Inventors: James Frank Brazdil, Glen Ellyn, IL (US); Richard J George, Oswego, IL (US); Bruce I Rosen, Park Ridge, IL (US)

(73) Assignee: BP Chemicals Limited, Middlesex (GB)

( * ) Notice: Subject to any disclaimer, the term of this patent is extended or adjusted under 35 U.S.C. 154(b) by 0 days.

(21) Appl. No.: 12/654,113

(22) Filed: Dec. 10, 2009

(65) Prior Publication Data

US 2010/0094047 A1   Apr. 15, 2010

Related U.S. Application Data

(62) Division of application No. 10/555,988, filed as application No. PCT/GB2004/001813 on Apr. 28, 2004, now abandoned.

(60) Provisional application No. 60/477,016, filed on Jun. 10, 2003.

(51) Int. Cl.
| | |
|---|---|
| *B01J 21/00* | (2006.01) |
| *B01J 23/00* | (2006.01) |
| *B01J 25/00* | (2006.01) |
| *B01J 29/00* | (2006.01) |
| *B01J 31/00* | (2006.01) |
| *B01J 21/04* | (2006.01) |
| *B01J 23/02* | (2006.01) |

(52) U.S. Cl. ........ 502/300; 502/100; 502/150; 502/305; 502/308; 502/311; 502/439

(58) Field of Classification Search .................. 562/542; 502/100, 150, 305, 308, 311, 439, 300
See application file for complete search history.

(56) References Cited

U.S. PATENT DOCUMENTS

| 4,250,346 A | 2/1981 | Young et al. |
| 4,524,236 A * | 6/1985 | McCain ..................... 585/658 |
| 2003/0088118 A1 | 5/2003 | Komada et al. |

FOREIGN PATENT DOCUMENTS

| EP | 0294846 | 10/1988 |
| EP | 1 346 766 A1 | 9/2003 |
| GB | 1 287 197 | 8/1972 |
| JP | 10-17523 | 1/1998 |
| WO | WO 02/51542 A1 | 4/2002 |

OTHER PUBLICATIONS

Derwent Publications Ltd., London GB; AN 1998-140953, XP-002287207.
Patent Abstracts of Japan, Publication No. 2002-088012, Publication Date Mar. 27, 2002, "Method for Producing (Meth)Acrylic Acid", 6 pgs.
Patent Abstracts of Japan, Publication No. 2002-088013, Publication Date Mar. 27, 2002, "Method for Producing (Meth)Acrylic Acid", 6 pgs.
Patent Abstracts of Japan, Publication No. 10-195036, Publication Date Jul. 28, 1998, "Vapor Phase Catalytic Oxidation Reaction of Hydrocarbon", 11 pgs.

* cited by examiner

*Primary Examiner* — James E McDonough
(74) *Attorney, Agent, or Firm* — Nixon & Vanderhye

(57) ABSTRACT

An oxide catalyst composition comprising the elements molybdenum, vanadium, niobium and titanium and a process for making the catalyst composition. A process for the selective oxidation of ethane and/or ethylene to acetic acid using the catalyst composition. The catalyst composition provides high selectivity to acetic acid with reduced selectivity to ethylene.

13 Claims, No Drawings

CATALYST COMPOSITION AND PROCESS FOR THE SELECTIVE OXIDATION OF ETHANE AND/OR ETHYLENE TO ACETIC ACID

This application is a divisional of application Ser. No. 10/555,988 filed 8 Nov. 2005, abandoned, which is a 371 of PCT/GB2004/001813 filed 28 Apr. 2004 which designated the U.S. and claims priority to Provisional Application No. 60/477,016 filed 10 Jun. 2003, the entire contents of each of which are hereby incorporated by reference.

The present invention relates to a catalyst composition for the selective oxidation of ethane to acetic acid and/or for the selective oxidation of ethylene to acetic acid, and to a process for the production of acetic acid utilizing the aforesaid catalyst composition.

Catalyst compositions comprising molybdenum, vanadium and niobium in combination with oxygen for use in processes for the production of acetic acid by the oxidation of ethane and/or ethylene are known in the art from, for example, U.S. Pat. No. 4,250,346, EP-A-1043064, WO 99/20592 and DE 196 30 832.

U.S. Pat. No. 4,250,346 discloses the oxidative dehydrogenation of ethane to ethylene and acetic acid in a gas phase reaction, at a temperature of less than about 550° C. using as a catalyst a composition comprising the elements molybdenum, X and Y in the ratio $Mo_a X_b Y_c$ wherein X is Cr, Mn, Nb, Ta, Ti, V and/or W, and preferably Mn, Nb, V and/or W; Y is Bi, Ce, Co, Cu, Fe, K, Mg, Ni, P, Pb, Sb, Si, Sn, Tl and/or U, and preferably Sb, Ce and/or U, a is 1, b is 0.05 to 1.0 and c is 0 to 2, and preferably 0.05 to 1.0, with the proviso that the total value of c for Co, Ni and/or Fe is less than 0.5.

WO 99/20592 relates to a method of selectively producing acetic acid from ethane, ethylene or mixtures thereof and oxygen at high temperature in the presence of a catalyst composition having the formula $Mo_a Pd_b X_c Y_d$ wherein X represents one or several of Cr, Mn, Nb, Ta, Ti, V, Te and W; Y represents one or several of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Nb, Zr, Hf, Ni, P, Pb, Sb, Si, Sn, Tl and U and a=1, b=0.0001 to 0.01, c=0.4 to 1 and d=0.005 to 1.

German patent application DE 196 30 832 A1 relates to a similar catalyst composition in which a=1, b>0, c>0 and d=0 to 2. Preferably, a=1, b=0.0001 to 0.5, c=0.1 to 1.0 and d=0 to 1.0.

The catalyst compositions of both WO 99/20592 and DE 19630832 require the presence of palladium.

EP-A-1043064 discloses a catalyst composition for the oxidation of ethane to ethylene and/or acetic acid and/or for the oxidation of ethylene to acetic acid which comprises in combination with oxygen the elements molybdenum, vanadium, niobium and gold in the absence of palladium according to the empirical formula:

$$Mo_a W_b Au_c V_d Nb_e Y_f \qquad (I)$$

wherein Y is one or more elements selected from the group consisting of: Cr, Mn, Ta, Ti, B, Al, Ga, In, Pt, Zn, Cd, Bi, Ce, Co, Rh, Ir, Cu, Ag, Fe, Ru, Os, K, Rb, Cs, Mg, Ca, Sr, Ba, Zr, Hf, Ni, P, Pb, Sb, Si, Sn, Tl, U, Re, Te and La; a, b, c, d, e and f represent the gram atom ratios of the elements such that: $0<a\leq1$; $0\leq b<1$ and $a+b=1$; $10^{-5}<c\leq0.02$; $0<d\leq2$; $0<e\leq1$; and $0\leq f\leq 2$.

There remains a need to develop a catalyst composition for the oxidation of ethane and/or ethylene to acetic acid with high selectivity to acetic acid and in which noble metals such as Pd and Au need not be used.

Surprisingly, it has now been found that by using a catalyst composition comprising molybdenum, vanadium, niobium and titanium in combination with oxygen, ethane and/or ethylene may be oxidized to acetic acid with increased selectivity to acetic acid. Furthermore, it has been found possible using the catalyst compositions of the present invention, to achieve a high selectivity to acetic acid with reduced selectivity to ethylene.

Accordingly, in a first aspect, the present invention provides a catalyst composition for the oxidation of ethane and/or ethylene to acetic acid, which composition comprises in combination with oxygen the elements molybdenum, vanadium, niobium and titanium according to the empirical formula:

$$Mo_a W_b Ti_c V_d Nb_e Y_f \qquad (I)$$

wherein Y is one or more elements selected from the group consisting of: Cr, Mn, Ta, B, Al, Ga, In, Pt, Zn, Cd, Bi, Ce, Co, Rh, Ir, Cu, Ag, Fe, Ru, Os, K, Rb, Cs, Mg, Ca, Sr, Ba, Zr, Hf, Ni, P, Pb, Sb, Si, Sn, Tl, U, Re, Te, La, Au and Pd;

a, b, c, d, e and f represent the pram atom ratios of the elements such that:
$0<a\leq1$; $0\leq b<1$ and $a+b=1$;
$0.05<c\leq2$;
$0<d\leq2$;
$0<e\leq1$; and
$0\leq f\leq 2$.

Catalyst compositions embraced within the formula (I) include:—

$Mo_a W_b Ti_c V_d Nb_e Y_f$
$Mo_a Ti_c V_d Nb_e Y_f$
$Mo_a W_b Ti_c V_d Nb_e$
$Mo_a Ti_c V_d Nb_e$

Preferably a>0.01. Preferably, d>0.1. Preferably, e>0.01. Preferably, e≤0.5. Preferably, f≥0.01. Preferably, f≤0.5.

Preferably, Y, when present, is selected from the group consisting of Bi, Ca, Ce, Cu, K, P, Sb, La and Te.

The catalyst compositions according to the present invention comprise a titanium component.

Advantageously high selectivities to acetic acid can be achieved using the catalyst compositions of the present invention in which the catalyst composition has a substantial absence of noble metals.

In one embodiment the catalyst compositions according to the present invention are substantially devoid of noble metals, such as Pd and/or Au.

A second aspect of the present invention relates to a process for the preparation of the catalyst compositions according to the first aspect of the present invention, comprising the steps of:

(a) forming a mixture comprising molybdenum, vanadium, niobium, titanium, optionally tungsten and optionally Y, in a solution;
(b) drying the mixture to form a dried solid material; and
(c) calcining the dried solid material to form the catalyst composition.

Suitably the mixture comprising molybdenum, vanadium, niobium, titanium, optionally tungsten and optionally Y may be formed by mixing compounds and/or complexes of each of the metals in a suitable solvent. The solvent is preferably water, and most preferably the mixture is a solution in Water having a pH in the range from 1 to 12, preferably from 2 to 8, at a temperature of from 20° to 100° C.

Preferably, the molybdenum is introduced in to the mixture in the form of ammonium salts such as ammonium heptamolybdate, or organic acids of molybdenum, such as acetates and oxalates. Other compounds of molybdenum which may be used include, for example, molybdenum oxides, molybdic acid and/or molybdenum chlorides.

Preferably, the vanadium is introduced in to the mixture in the form of ammonium salts, such as ammonium metavanadate or ammonium decavanadate, or organic acids of vanadium, such as acetates and oxalates. Other compounds of vanadium which may be used include, for example, as vanadium oxides and sulphates.

Preferably, the niobium is introduced in to the mixture in the form of ammonium salts, such as ammonium niobium oxalate. Other compounds of niobium, such as niobium chlorides, may also be used, preferably complexed with an oxalate, a carboxylic acid or similar coordinating compound to improve solubility.

Preferably, the titanium component of the catalyst composition is introduced to the mixture in the form of a soluble or reactive precursor, such as a halide or alkoxide. More preferably, the titanium component of the catalyst composition is introduced to the mixture as a titanium alkoxide, most preferably as titanium isopropoxide.

Generally, the mixture of compounds containing the elements is prepared by dissolving sufficient quantities of soluble compounds and dispersing any insoluble compounds so as to provide a desired gram-atom ratio of the elements in the catalyst composition. The solvent is removed from the mixture by drying, preferably by spray-drying, to form a dried solid material. This dried solid material is then calcined to form the catalyst composition. Calcination is preferably performed by heating to a temperature of from 200 to 550° C., suitably in air or oxygen, for a period of from 1 minute to 24 hours.

The catalyst composition of the present invention may be used unsupported or supported. Suitable supports include silica, alumina, titania, titanosilicates, zirconia, silicon carbide and mixtures of two or more thereof, preferably silica. Titanium may be present in a supported catalyst composition both as a component of the catalyst composition on the support, and as a component of the support itself, such as a titania support or as part of a support comprising titanium, for example as part of a mixed support comprising both titania and silica supports, or as part of a titanosilicate support.

When used on a support, the catalyst composition typically comprises at least about 10% and/or up to about 80% by weight of the total weight of the catalyst composition and the support (with the remainder being the support material). Preferably the catalyst composition comprises at least 40 wt % of the total weight of the catalyst composition and the support and/or up to 60 wt % of the total weight of the catalyst composition and the support.

When used on a support, the supported catalyst composition may be prepared according to the process of the second aspect of the present invention by addition of the a support material or a suitable precursor thereof, such as a sol, for example, a silica sol, to the mixture comprising molybdenum, vanadium, niobium, titanium, optionally tungsten and optionally Y. The support material or suitable precursor thereof may be added at any suitable stage, such as, for example, during drying, such as after a partial drying, of the mixture. Preferably, the support material or suitable precursor thereof is introduced to the mixture prior to drying the mixture in step (b), most preferably by introducing the support material or suitable precursor thereof during formation of the mixture in step (a), such that said support material or suitable precursor thereof forms a component of said mixture formed in step (a).

Further details of a suitable method for preparing a catalyst composition may be found in, for example, EP-A-0166438, the contents of which are herein incorporated by reference.

In a third aspect of the present invention there is provided a process for the selective production of acetic acid from a gaseous mixture comprising ethane and/or ethylene which process comprises contacting the gaseous mixture with a molecular oxygen-containing gas at elevated temperature in the presence of a catalyst composition as hereinbefore described.

The feed gas comprises ethane and/or ethylene, preferably ethane.

Ethane and/or ethylene may each be used in substantially pure form or admixed with one or more of nitrogen, methane, carbon dioxide and water in the form of steam, which may be present in major amounts, for example greater than 5 volume percent or one or more of hydrogen, carbon monoxide, $C_3/C_4$ alkenes and alkenes, which may be present in minor amounts, for example less than 5 volume percent.

The molecular oxygen-containing gas may be air or a gas richer or poorer in molecular oxygen than air, for example oxygen. A suitable gas may be, for example, oxygen diluted with a suitable diluent, for example nitrogen.

It is preferred to feed, in addition to ethane and/or ethylene and the molecular oxygen-containing gas, water (steam) because this can improve the selectivity to acetic acid.

The elevated temperature may suitably be in the range from 200 to 500° C., preferably from 200 to 400° C.

The pressure may suitably be atmospheric or superatmospheric, for example in the range from 1 to 50 bar, preferably from 1 to 30 bar.

The process of the third aspect may be a fixed bed or a fluidised bed process.

Operating conditions and other information applicable to the performance of the invention may be found in the aforesaid prior art, for example U.S. Pat. No. 4,250,346.

Using the catalyst compositions of the present invention, a high selectivity to acetic acid may be achieved in combination with a low, if any, selectivity to ethylene. Typically, using the catalyst compositions of the present invention, the selectivity to acetic acid is at least 50 mol %, preferably at least 55 mol %, and most preferably at least 60 mol %.

Typically, using the catalyst compositions of the present invention, the selectivity to ethylene is less than 30 mol %, preferably less than 20 mol %, and most preferably less than 10 mol %.

Preferably, using the catalyst compositions of the present invention, the selectivity to acetic acid is at least 60 mol % and the selectivity to ethylene is less than 10 mol %.

As used herein, selectivity refers to a percentage that reflects the amount of desired acetic acid product produced as compared to the total carbon in the products formed:—

% selectivity=100*Moles of acetic acid produced/$S$ wherein S=the molar acid-equivalent sum (carbon basis) of all carbon-containing products, excluding the alkane in the effluent.

The process of the invention will now be further illustrated by reference to the following Examples.

CATALYST PREPARATION

Examples According to the Present Invention

Catalyst A: $Mo_{1.00}V_{0.529}Nb_{0.124}Au_{0.0012}Ti_{0.331}O_x$

The following three solutions were prepared:

Solution A: 214 g of ammonium heptamolybdate was dissolved in 250 g of water at 45° C. with stirring.

Solution B: 75 g of ammonium metavanadate was added to 725 g of water in a 2-liter beaker and heated to 80° C. The ammonium metavanadate did not completely dissolve.

Solution C: 74 g of ammonium niobium oxalate was added to 275 g of water in a 6-liter stainless steel beaker and heated to 45° C. A sol formed within 30 minutes.

Solution C was added to solution B and allowed to digest at 80° C. for 30 minutes.

Solution A was then added to the mixture of solution C and solution B, and then stirred for 15 minutes at medium heat to give a slurry. 0.425 g $AuCl_3$ were then added to the slurry to give a slurry containing Mo, V, Nb and Au. 638 grams of silica sol (Nalco 41D01) were then added to the stirred slurry. 111 grams of titanium isopropoxide were dripped into the slurry at 50° C. Percent solids was adjusted to ~36%. The slurry was homogenized at 10,000 rpm for approximately 2 minutes. Spray drying was carried out in a mini-Niro spray-drier immediately after the solution was homogenized to form a spray-dried supported catalyst composition. The spray drying conditions used were as follows: an inlet temperature of 290° C. inlet and an outlet temperature of 138° C. The spray-dried supported catalyst composition was then calcined in air for 3 hours at 375° C. in a static muffle furnace. The resultant spray-dried supported catalyst composition (Catalyst A) had a nominal composition $Mo_{60.5}V_{32}Nb_{7.5}Au_{0.07}Ti_{20}O_x$ on silica, and at a nominal metal loading of 44% of the total catalyst weight. The supported catalyst composition had a surface area of 32 m²/g and a density of 1.15 g/cm³.

Catalyst B: $Mo_{1.00}V_{0.529}Nb_{0.124}Ti_{0.331}O_x$

Catalyst B had a similar nominal composition as Catalyst A but without the addition of gold. Catalyst B was prepared as described for Catalyst A, but without the addition of $AuCl_3$. The spray-dried supported catalyst composition B had a nominal composition $Mo_{60.5}V_{32}Nb_{7.5}Ti_{20}O_x$ on silica, and at a nominal metal loading of 44% of the total catalyst weight. The supported catalyst composition B had a density of 1.16 g/cm³ (and was expected to have a surface area of approximately 30 m²/g (not measured)).

Examples not According to the Present Invention

Comparative Catalyst 1: $Mo_{1.00}V_{0.529}Nb_{0.124}O_x$

Comparative Catalyst 1 had a similar nominal composition to Catalysts A and B but without the addition of gold or titanium. Comparative catalyst 1 was prepared as described for Catalyst A, but without the addition of $AuCl_3$ or titanium isopropoxide.

The resultant spray-dried supported catalyst composition had a nominal composition $Mo_{60.5}V_{32}Nb_{7.5}O_x$ on silica, and at a nominal metal loading of 50% of the total catalyst weight. The supported catalyst composition had a surface area of 28 m²/g and a density of 1.2 g/cm³.

Comparative Catalyst 2: $Mo_{1.00}V_{0.529}Nb_{0.124}Au_{0.0012}O_x$

Comparative Catalyst 2 had a similar nominal composition to Catalyst A but without the addition of titanium. Comparative catalyst 2 was prepared as described for Catalyst A, but without the addition of titanium isopropoxide.

The resultant spray-dried supported catalyst composition had a nominal composition $Mo_{60.5}V_{32}Nb_{7.5}Au_{0.07}O_x$ on silica, and at a nominal metal loading of 50% of the total catalyst weight. The supported catalyst composition had a surface area of 36 m²/g and a density of 1.21 g/cm³.

Comparative Catalyst 3; $Mo_{1.00}V_{0.529}Nb_{0.124}Au_{0.0012}Pd_{0.0001}O_x$

Comparative Catalyst 3 had a similar nominal composition to Comparative Catalyst 2 except that a palladium component was added. Comparative catalyst 3 was prepared as described for Catalyst A except that 0.0124 g of palladium (IV) chloride was added directly after the gold (III) chloride and without the addition of titanium isopropoxide.

The resultant spray-dried supported catalyst composition had a nominal composition $Mo_{60.5}V_{32}Nb_{7.5}Au_{0.07}Pd_{0.007}O_x$ on silica, and at a nominal metal loading of 50% of the total catalyst weight. The supported catalyst composition had a surface area of 24 m²/g and a density of 1.23 g/cm³.

Catalyst Testing

The catalyst to be tested was sieved to obtain a specific particle size distribution (psd) of 70% 230/325 mesh (50/50), 25% pans (fines) and 5% greater than 170 mesh. 10 grams of catalyst and an inert diluent with the same particle size distribution (St Gobain SA 539 alpha alumina, 43 g, density 1.27 g/ml) were added into a 40 cc fluidised bed reactor. The reaction was typically performed at a temperature between 310° C. and 320° C. and at a reaction pressure of 16 barg. Ethane, ethylene (to mimic a recycle of ethylene), nitrogen and oxygen mixture was fed to the reactor using Brooks Mass Flow Controllers. Water was added by vaporisation and mixing with these feed gases prior to the reaction zone. The volatile reactor effluent was sampled and analysed by gas liquid chromatography. The water and acetic acid were condensed and analysed by gas liquid chromatography. The reactor bed temperature was monitored by a moving thermocouple.

Results

Example A

Catalyst A was tested under the conditions in Table A below:

TABLE A

| | | | | Run Conditions (Feed mol %) | | | | |
|---|---|---|---|---|---|---|---|---|
| Pressure Barg | Max T ° C. | Total Flow ml/min | GHSV h-1 | $C_2H_6$ | $C_2H_4$ | $H_2O$ | $O_2$ | $N_2$ |
| 16 | 311-316 | 428 | 3240 | 60.2 | 5.2 | 5.0 | 6.5 | 23.3 |

During the test there was an initial period during which the acetic acid space-time yield (STY) and oxygen conversion increased whilst the ethylene STY decreased. After this period Catalyst A settled down to produce acetic acid and low levels of ethylene. The averaged selectivity data between 100-180 hours on stream is presented in Table 1 below.

Example B

Catalyst B was tested under the conditions in Table B below:

TABLE B

| | | | | Run Conditions (Feed mol %) | | | | | |
|---|---|---|---|---|---|---|---|---|---|
| Pressure Barg | Max T °C. | Total Flow ml/min | GHSV h-1 | $C_2H_6$ | $C_2H_4$ | $H_2O$ | $O_2$ | $N_2$ | |
| 16 | 310-320 | 428 | 3200 | 60.2 | 5.0 | 5.0 | 6.5 | 23.3 | |

Catalyst B showed a similar profile to Catalyst A, in that during the test there was an initial period during which acetic acid space-time yield (STY) and oxygen conversion increased whilst the ethylene STY decreased after which Catalyst B settled down to produce acetic acid with only low levels of ethylene. The averaged selectivity data between 100-180 hours on stream is presented in Table 1 below.

Comparative Catalysts

Comparative Catalysts 1 to 3 were tested under similar conditions to Catalysts A and B. The averaged selectivity data is presented in Table 1 below.

TABLE 1

| Example | Acetic acid selectivity | Ethylene selectivity | COx selectivity |
|---|---|---|---|
| Example A (Catalyst A) | 56% | 14% | 29% |
| Example B (Catalyst B) | 62% | 5% | 35% |
| Comparative Catalyst 1 | 32% | 58% | 10% |
| Comparative catalyst 2 | 33% | 56% | 11% |
| Comparative catalyst 3 | 50% | 34% | 16% |

From Table 1 it can be seen that using the catalyst compositions of the present invention, a high selectivity to acetic acid may be achieved in combination with a reduced selectivity to ethylene. The data for Catalyst B shows that advantageously high selectivities to acetic acid can be achieved using catalyst compositions of the present invention in which noble metals such as Pd and Au are not present.

The invention claimed is:

1. A process for the selective production of acetic acid from a gaseous mixture comprising ethane and/or ethylene which process consists essentially of contacting the gaseous mixture with a molecular oxygen-containing gas at elevated temperature in the presence of a catalyst composition which composition consists of in combination with oxygen the elements molybdenum, vanadium, niobium and titanium according to the empirical formula:

$$Mo_a W_b Ti_c V_d Nb_e Y_f \quad (I)$$

wherein Y is one or more elements selected from the group consisting of: Cr, Ta, B, Al, Ga, In, Pt, Zn, Cd, Bi, Ce, Co, Rh, Ir, Cu, Ag, Fe, Ru, Os, K, Rb, Cs, Mg, Ca, Sr, Ba, Zr, Hf, Ni, P, Pb, Si, Sn, Tl, U, Re, La, Au and Pd;

a, b, c, d, e and f represent the gram atom ratios of the elements such that:

$0 < a \leq 1$; $0 \leq b < 1$ and $a+b=1$;
$0.05 < c \leq 2$;
$0 < d \leq 2$;
$0 < e \leq 1$; and
$0 \leq f \leq 2$, wherein the selectivity to ethylene is less than 20 mol % and wherein the selectivity to acetic acid is at least 50 mol %.

2. A process as claimed in claim 1 wherein formula (I) is selected from the group consisting of $Mo_a W_b Ti_c V_d Nb_e Y_f$; $Mo_a Ti_c V_d Nb_e Y_f$; $Mo_a W_b Ti_c V_d Nb_e$ and $Mo_a Ti_c V_d Nb_e$.

3. A process as claimed in claim 1 wherein Y is selected from the group consisting of Bi, Ca, Ce, Cu, K, P and La.

4. A process as claimed in claim 1 wherein the catalyst composition has the formula $Mo_{1.00}V_{0.529}Nb_{0.124}Au_{0.0012}Ti_{0.331}O_x$ or $Mo_{1.00}V_{0.529}Nb_{0.124}Ti_{0.331}O_x$, wherein x is a number which satisfies the valencies of the elements in the composition for oxygen.

5. A process according to claim 1 in which the catalyst composition has a substantial absence of noble metals.

6. A process according to claim 1 wherein the catalyst composition is a supported catalyst.

7. A process according to claim 6 wherein the support is selected from the group consisting of silica, alumina, a titanium-containing support, titania, titanosilicates, zirconia, silicon carbide and mixtures thereof.

8. A process according to claim 7 wherein the support is selected from the group consisting of silica, a titanium-containing support and mixtures thereof.

9. A process according to claim 1 in which ethane and optionally ethylene is oxidised to acetic acid.

10. A process according to claim 1 in which the gaseous mixture is contacted with the molecular oxygen-containing gas in the presence of water.

11. A process according to claim 1 wherein the process is a fixed bed or fluidised bed process.

12. A process according to claim 1 wherein the selectivity to acetic acid is at least 60 mol %.

13. A process according to claim 1 wherein the selectivity to ethylene is less than 10 mol %.

* * * * *